(12) United States Patent
Miette et al.

(10) Patent No.: US 11,039,781 B2
(45) Date of Patent: Jun. 22, 2021

(54) NON-INVASIVE DEVICE FOR DETECTING LIVER DAMAGE

(71) Applicant: ECHOSENS, Paris (FR)

(72) Inventors: Véronique Miette, Villejuif (FR); Laurent Sandrin, Bourg-la-Reine (FR); Magali Sasso, Bellegarde (FR)

(73) Assignee: ECHOSENS, Paris (FR)

( * ) Notice: Subject to any disclaimer, the term of this patent is extended or adjusted under 35 U.S.C. 154(b) by 688 days.

(21) Appl. No.: 15/579,016

(22) PCT Filed: Jun. 1, 2016

(86) PCT No.: PCT/EP2016/062392
§ 371 (c)(1),
(2) Date: Dec. 1, 2017

(87) PCT Pub. No.: WO2016/193312
PCT Pub. Date: Dec. 8, 2016

(65) Prior Publication Data
US 2018/0140247 A1 May 24, 2018

(30) Foreign Application Priority Data

Jun. 2, 2015 (FR) ........................ 1554995

(51) Int. Cl.
*A61B 5/00* (2006.01)
*A61B 8/08* (2006.01)

(52) U.S. Cl.
CPC .......... *A61B 5/4244* (2013.01); *A61B 5/4842* (2013.01); *A61B 5/7264* (2013.01); *A61B 5/7275* (2013.01); *A61B 8/08* (2013.01); *A61B 8/485* (2013.01); *A61B 8/5223* (2013.01)

(58) Field of Classification Search
None
See application file for complete search history.

(56) References Cited

U.S. PATENT DOCUMENTS

2005/0203398 A1* 9/2005 Sandrin ................ A61B 8/485
600/438
2008/0249408 A1* 10/2008 Palmeri ................ A61B 8/485
600/438

(Continued)

FOREIGN PATENT DOCUMENTS

FR   2 843 290 A1   2/2004
FR   2 949 965 A1   3/2011
(Continued)

OTHER PUBLICATIONS

Ludovico Abenavoli, "Transient Elastography for Assessment of Non-Alcoholic Fatty Liver Disease", Liver Biopsy, pp. 283-292, 2011 (Year: 2011).*

(Continued)

*Primary Examiner* — Joanne M Hoffman
(74) *Attorney, Agent, or Firm* — Pillsbury Winthrop Shaw Pittman LLP

(57) ABSTRACT

A device calculates a score reflecting a state of liver damage, the calculating device being designed to calculate a score using the following physical parameters: a parameter corresponding to inflammation and/or fibrosis; and a parameter corresponding to steatosis.

17 Claims, 2 Drawing Sheets

(56) References Cited

U.S. PATENT DOCUMENTS

| | | | | |
|---|---|---|---|---|
| 2010/0069751 | A1* | 3/2010 | Hazard | G01S 7/52042 |
| | | | | 600/438 |
| 2012/0128223 | A1* | 5/2012 | Rivaz | A61B 8/485 |
| | | | | 382/131 |
| 2012/0158323 | A1* | 6/2012 | Hazard | A61B 8/485 |
| | | | | 702/56 |
| 2012/0190983 | A1* | 7/2012 | Sandrin | A61B 8/08 |
| | | | | 600/442 |
| 2013/0028536 | A1* | 1/2013 | Hazard | A61B 8/5276 |
| | | | | 382/275 |
| 2014/0148697 | A1* | 5/2014 | Barry | A61B 8/5223 |
| | | | | 600/438 |
| 2014/0170741 | A1* | 6/2014 | Wang | G16B 40/00 |
| | | | | 435/288.7 |
| 2014/0316267 | A1* | 10/2014 | Barry | A61B 8/085 |
| | | | | 600/438 |
| 2015/0209013 | A1* | 7/2015 | Tsymbalenko | A61B 8/483 |
| | | | | 600/440 |
| 2015/0305717 | A1* | 10/2015 | Hollender | A61B 8/4494 |
| | | | | 600/438 |
| 2015/0327835 | A1* | 11/2015 | Kim | A61B 8/5223 |
| | | | | 600/438 |

FOREIGN PATENT DOCUMENTS

| | | |
|---|---|---|
| WO | WO 2013/025798 A1 | 2/2013 |
| WO | WO 2015/014763 A2 | 2/2015 |

OTHER PUBLICATIONS

Jamali, R., "Non-Alcoholic Fatty Liver Disease: Diagnosis and Evaluation of Disease Severity," Thrita., Dec. 2013, vol. 2, No. 4, pp. 43-51.

Pearce, S. G., et al., "Noninvasive biornarkers for the diagnosis of steatohepatitis and advanced fibrosis in NAFLD," Biomarker Research 2013, 1:7, 11 pages.

International Search Report as issued in International Patent Application No. PCT/EP2016/062392, dated Aug. 17, 2016.

* cited by examiner

NON-INVASIVE DEVICE FOR DETECTING LIVER DAMAGE

CROSS-REFERENCE TO RELATED APPLICATIONS

This is the U.S. National Stage of PCT/EP2016/062392, filed Jun. 1, 2016, which in turn claims priority to French Patent Application No. 1554995, filed Jun. 2, 2015, the entire contents of all applications are incorporated herein by reference in their entireties.

TECHNICAL FIELD

The invention relates to a non-invasive device for detecting liver damage using ultrasonic waves and shear waves. Said device may be used for humans and animals and is for example intended for the detection of liver damage of ASH (Alcoholic SteatoHepatitis) or NASH (Non-Alcoholic SteatoHepatitis) type. The invention also pertains to a score reflecting liver damage.

PRIOR ART

Normally, chronic liver tissue diseases cause liver damage such as fibrosis. Fibrosis is a process of fibrous healing of liver tissue resulting from inflammation. The initially asymptomatic fibrosis may evolve into cirrhosis. The elasticity of liver tissue constitutes a marker of liver fibrosis. In order to measure and quantify the elasticity of liver tissue, it is known to use pulse elastography, as described, for example, in the patent application number FR 2843290.

This document describes an embodiment of a device according to the prior art. This device is composed of a probe provided with a vibration generator generating a low frequency elastic wave in a tissue, for example by vibration, and analysing the propagation of this low frequency elastic wave by means of high frequency ultrasonic waves transmitted and received by an ultrasonic transducer. The measurements obtained via this device make it possible to quantify the elasticity of liver tissue. This device also makes it possible to quantify the ultrasonic attenuation of tissues, as described, for example, in the patent application number FR 2949965. The quantification of ultrasonic attenuation in the liver corresponds to the amount of steatosis.

On the other hand, in humans certain diseases, for example NASH, are not necessarily linked only to the sole amount of fibrosis or to the sole amount of steatosis, and may for example associate steatosis type damage (presence of fat in the liver) and inflammation with or without fibrosis. Consequently, the stage of NASH or the evolution towards NASH cannot be diagnosed using a single parameter.

DESCRIPTION OF THE INVENTION

The present invention aims to resolve at least one of the aforesaid drawbacks of the prior art. To do so, the invention proposes a non-invasive device for detecting liver damage taking into account different parameters. The invention also proposes a score reflecting a type of liver damage.

To this end, one aspect of the invention relates to a device for calculating a score for humans or animals, said score being a quantitative or semi-quantitative evaluation of liver damage of alcoholic or non-alcoholic steatohepatitis type, said calculating device being constructed and arranged to calculate a score using the following at least physical or even biological parameters:

a parameter corresponding to inflammation and/or fibrosis, a parameter corresponding to steatosis.

This embodiment particularly has the advantage of enabling early detection of certain types of liver damage, such as for example NASH, NASH being able to correspond to inflammation, fibrosis and steatosis. On the other hand, NAFLD (Non-Alcoholic Fatty Liver Disease) simply corresponds to steatosis. Thanks to the score, it is thus possible to differentiate patients suffering from a NAFLD type disease from patients suffering from a NASH type disease.

In one non-limiting embodiment of the device according to the invention, the score is a quantitative or semi-quantitative evaluation (for example, binary indicator) of liver damage of alcoholic or non-alcoholic steatohepatitis type.

In one non-limiting embodiment of the calculating device according to the invention, the calculating device is integrated in:

an ultrasound scanner, or a device constructed and arranged to measure at least liver elasticity.

In one non-limiting embodiment, the device according to the invention is constructed and arranged to deliver the score concurrently with the measured physical parameters. In other words, the ultrasound scanner or the device constructed and arranged to measure at least liver elasticity measures physical parameters and the device according to the invention calculates the score while taking into account at least the measured physical parameters.

In one non-limiting embodiment of the calculating device according to the invention, the calculating device is constructed and arranged to communicate with:

a remote ultrasound scanner, or a remote device constructed and arranged to measure at least liver elasticity.

In one non-limiting embodiment of the device according to the invention, the parameter corresponding to fibrosis is elasticity.

In one non-limiting embodiment of the device according to the invention, the parameter corresponding to steatosis is a measurement of the attenuation of ultrasonic waves, for example the parameter called CAP as described in the article Sasso, M., et al. (2010). "Controlled attenuation parameter (CAP): a novel VCTE guided ultrasonic attenuation measurement for the evaluation of hepatic steatosis: preliminary study and validation in a cohort of patients with chronic liver disease from various causes." Ultrasound Med Biol 36(11): 1825-1835.

In one non-limiting embodiment of the device according to the invention, the parameter corresponding to steatosis is a measurement of liver tissue viscosity.

In one non-limiting embodiment of the device according to the invention, the calculating device is constructed and arranged to calculate a score using at least one additional parameter corresponding to inflammatory activity. For example, this parameter may be the transaminase value, ALAT, ASAT, GGT, liver elasticity or liver viscosity.

In one non-limiting embodiment of the device according to the invention, the calculating device is constructed and arranged to calculate a score using at least one additional parameter corresponding to metabolic syndrome.

In one non-limiting embodiment of the device according to the invention, the calculating device is constructed and arranged to calculate a score using at least one additional parameter of anthropomorphic type.

In one non-limiting embodiment of the device according to the invention, the calculating device is constructed and arranged to calculate a score using at least one additional parameter of biological type. The at least one biological parameter may for example be selected from the following parameters: transaminases (ASAT, ALAT), GGT, PAL, serum iron, ferritin, transferrin saturation, adipokine (for example, adiponectin, leptin, resistin), cytokine (for example, TNFa, IL6, IL1 -(3), HDL cholesterol, glycaemia, insulinemia, bilirubin, a2macroglobulin, haptoglobin, apolipoprotein A1, CK18, triglycerides, adiponectin, urea, genetic polymorphism (for example: PNPLA3, TM6SF2 polymorphism), CRP and/or leptin.

In one non-limiting embodiment of the device according to the invention, the calculating device is constructed and arranged to communicate with a device for displaying the score. The score may be displayed in the form of a numerical value, a binary indicator, a probability or a risk. This embodiment particularly has the advantage of enabling simplicity of interpretation of the analysis of the score reflecting a calculated state of liver damage.

One aspect of the invention also pertains to a score taking into account the following physical or even biological parameters:
 a parameter corresponding to inflammation and/or fibrosis, and
 a parameter corresponding to steatosis.

In one non-limiting embodiment, the score takes into account at least one parameter of inflammatory activity. The at least one parameter of inflammatory activity may be selected from the following parameters: the transaminase value, liver elasticity or liver viscosity.

In one non-limiting embodiment, the score takes into account at least one anthropomorphic parameter of weight, height, waist circumference, hip circumference, chest girth type or a demographic parameter of age and sex type.

In one non-limiting embodiment, the score takes into account at least one biological parameter.

The at least one biological parameter may be selected from the following parameters: transaminases (ASAT, ALAT), GGT, PAL, serum iron, ferritin, transferrin saturation, adipokine (for example, adiponectin, leptin, resistin) cytokine (for example, TNFa, IL6, IL1 -(3), cholesterol, HDL cholesterol, glycaemia, insulinemia, bilirubin, a2macroglobulin, haptoglobin, apolipoprotein A1, CK18, triglycerides, adiponectin, urea, genetic polymorphism (for example: PNPLA3, TM6SF2 polymorphism), CRP and/or leptin.

The biological parameter may be a metabolomic parameter.

In one non-limiting embodiment, the score is calculated using statistical modelling (also called statistical learning) of the type logistic regression, decision trees, Bayes classifiers, random forests, WMS, neural networks, discriminatory analysis, etc.

BRIEF DESCRIPTION OF THE FIGURES

Other characteristics and advantages of the invention will become clear from the description that is given thereof below, for indicative purposes and in no way limiting, with reference:
 to FIG. 1 illustrating, in a schematic manner, a first exemplary embodiment of a device for calculating a score reflecting a state of liver damage integrated in a device constructed and arranged to measure liver elasticity,
 to FIG. 2 illustrating, in a schematic manner, a second exemplary embodiment of a device for calculating a score reflecting a state of liver damage constructed and arranged to communicate with a remote ultrasound scanner.
 to FIG. 3 illustrating, in a schematic manner, a third exemplary embodiment of a device for calculating a score reflecting a state of liver damage constructed and arranged to communicate with a remote ultrasound scanner.

DESCRIPTION OF THE INVENTION

Figure 1:
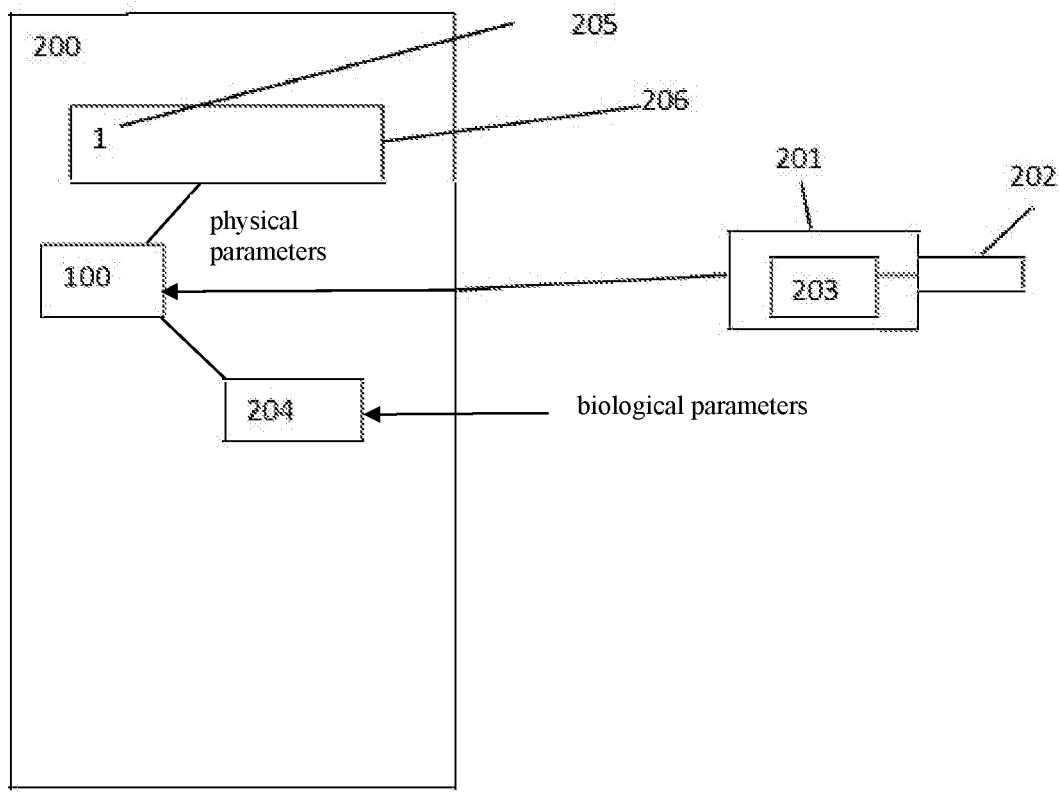

FIG. 1 represents a device 100 for calculating a score reflecting a state of liver damage integrated in a device 200 constructed and arranged to measure liver elasticity.

In this non-limiting embodiment, the device 200 comprises an elastography probe 201 provided with an ultrasonic transducer 202 constructed and arranged to transmit and receive ultrasonic waves. In this embodiment, the elastography probe 201 further comprises means for generating a shear wave in the liver tissue. Said means may be an electrodynamic actuator 203 constructed and arranged to generate a low frequency wave. The device 200 is thus constructed and arranged to measure physical parameters, for example parameters which correspond to inflammation and/or fibrosis and parameters which correspond to steatosis.

As an example, a parameter linked to fibrosis may be the elasticity of the liver. This elasticity measurement constitutes a marker of the pathological state of the liver tissue.

The parameter corresponding to steatosis may be a measurement of the attenuation of ultrasonic waves in the liver tissue. Liver steatosis is an accumulation of fat in the liver. The measurement of the attenuation of the propagation of ultrasonic waves thus makes it possible to quantify steatosis.

The device 100 for calculating a score reflecting a state of liver damage is constructed and arranged to calculate a score using a parameter corresponding to inflammation of liver tissue and/or a parameter corresponding to fibrosis. In the example described, these parameters are measured using the device 200 together with the elastography probe 201 and received by the device 100.

In the example illustrated, the device 200 also comprises a human-machine interface 204 constructed and arranged to enter metabolic syndrome marker parameters used to calculate the score.

Thus, an operator may enter, via the human-machine interface 204, metabolic syndrome marker parameters. Metabolic syndrome is taken to mean the association of a series of health problems having in common poor corporal metabolism, it is a grouping together of risk factors more or less linked by a common origin, metabolic targets or mechanisms. This group of parameters may thereby comprise: HDL cholesterol, triglycerides, glycaemia, arterial pressure, and/or the waist circumference.

This human-machine interface 204 is also constructed and arranged to enter biological parameters used to calculate the score. These biological parameters may be: transaminases (ALAT, ASAT), GGT, PAL, serum iron, cholesterol, HDL cholesterol, glycaemia, insulinemia, bilirubin, a2macroglobulin, haptoglobin, apolipoprotein A1, CK18, triglycerides, adiponectin, and/or leptin.

This human-machine interface 204 is also constructed and arranged to enter demographic and anthropomorphic parameters used to calculate the score. These demographic and anthropomorphic parameters are for example formed by the age, the sex, the height, the weight, the waist circumference, the hip circumference or the chest girth of an individual.

As a function of these different parameters, the calculating device 100 calculates a score using a logistic regression or any other scoring method, for example of the type decision trees, Bayes classifiers, random forests, wide margin separator (WMS) decision trees, or instead neural networks.

To this end, the calculating device 100 may be formed by one or more microprocessors constructed and arranged to execute sequences of instructions enabling the implementation of the aforesaid logistic regression or any other scoring method.

Figure 3:
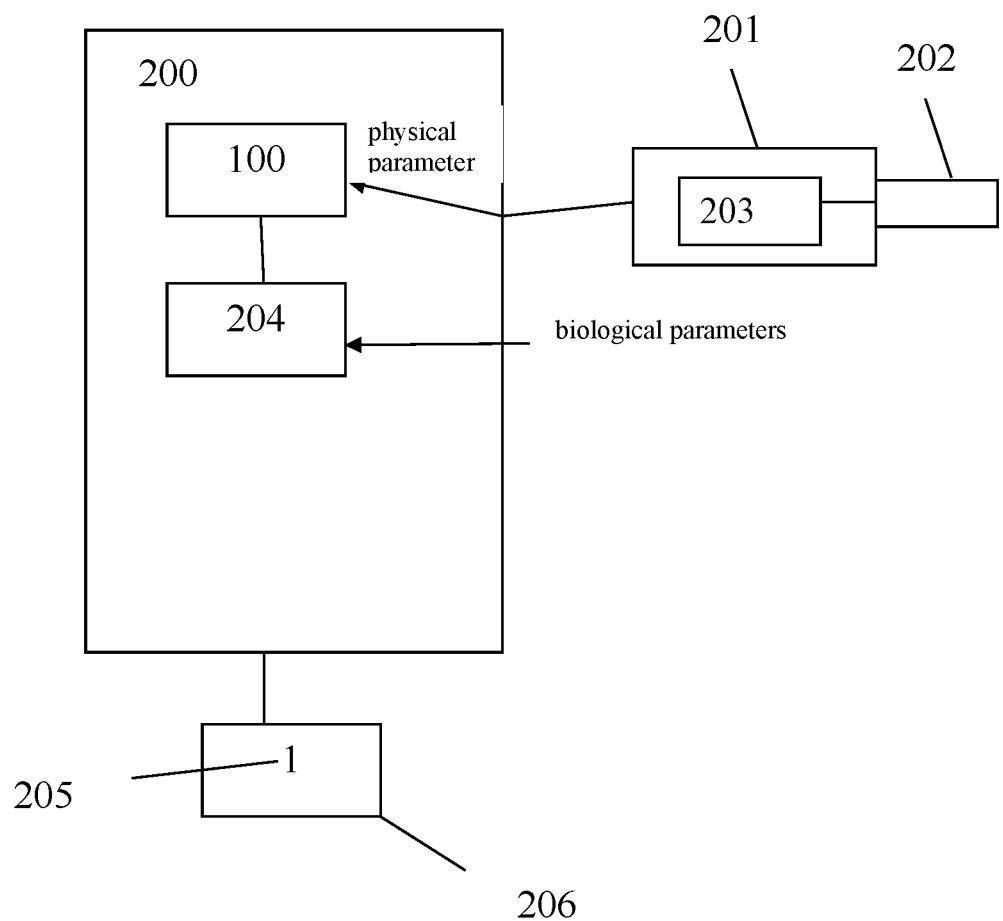

In the example illustrated of FIG. 1, the calculated score is represented in the form of a binary indicator 205 equal to 1 and displayed on a screen 206 of the device 200. This binary indicator 205 may be used to advise a patient to consult a specialist. For example, when the indicator is equal to 1, the patient is diagnosed as being at risk and requires a more detailed investigation or additional examinations have to be carried out. In the embodiment of FIG. 3, the screen 206 is positioned remotely from the calculating device 100 and the device 200 that comprises the elastography probe 201.

In contrast, when the indicator is equal to 0, the patient does not need to consult a specialist. This indicator may also be different, it may be implemented in the form of a value.

In this non-limiting embodiment, the measurements of physical parameters, the input of other parameters, the calculation of the score and the display of the score are carried out in the device 200. Thus, this embodiment particularly has the advantage of calculating in real time the score (in other words at the place where the measurements of the physical parameters are carried out), then displaying the score enabling rapidity of analysis.

In different non-limiting examples, the device 200 may be formed by an ultrasound scanner, an MRI, or an MRI implementing magnetic resonance elastography (MRE).

Figure 2:
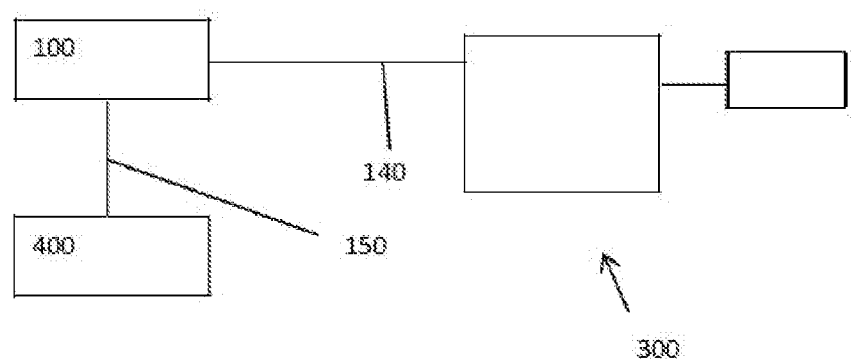

In one non-limiting embodiment illustrated in FIG. 2, the device for calculating a score reflecting a state of liver damage 100 is constructed and arranged to communicate with a remote ultrasound scanner 300. In other words, the calculating device 100 is remote vis-a-vis the ultrasound scanner 300. Thus, the measurements are carried out on the ultrasound scanner 300 then transmitted via a network link 140, for example an Ethernet or Bluetooth or Wi-Fi type link, to the calculating device 100. It is also possible to transmit other parameters, for example of anthropomorphic or demographic type, to the calculating device 100 via a computer 400. Similarly, this computer 400 may communicate with the calculating device 100 via an Ethernet or Wi-Fi link 150. The calculating device 100 may be materialised by one or more processors. Furthermore, the computer may be integrated in the ultrasound scanner 300.

In this non-limiting embodiment, the score may be displayed on the ultrasound scanner 300, on the computer 400 or both.

The invention claimed is:

1. A system for calculating a score in a patient, said score being a quantitative or semi-quantitative evaluation of liver damage of alcoholic or non-alcoholic steatohepatitis type, said system comprising:
   a) an elastography device configured to carry out measurements of physical parameters of the patient, the elastography device configured to generate a shear wave, the elastography device including
      an ultrasonic transducer configured to emit ultrasound shots and to receive corresponding echo signals to track how biological tissues of the patient are moved by the shear wave, the physical parameters including at least liver stiffness and liver ultrasound attenuation associated with the biological tissues,
   b) a calculating device in communication with the elastography device and configured to receive values of said physical parameters from the elastography device and a value of one or more biological parameters, the one or more biological parameters including at least one transaminase (ASAT or ALAT), said calculating device including one or more processors configured to execute a sequence of instructions for determining a score parameter, based on the values of the physical parameters and the one or more biological parameters, representative of liver damage in said patient, and
   c) a display in communication with said calculating device, said display configured to display the score parameter, the score parameter being displayed in the form of a numerical value, a binary indicator, a probability or a risk, said score parameter providing an estimate of NASH.

2. The system according to claim 1, wherein the sequence of instructions determine the score parameter according to a logistic regression, a decision tree, a Bayes classifier, or a random forest regression.

3. The system according to claim 1, wherein the calculating device is integrated in a device that includes the elastography device and the display.

4. The system according to claim 3, wherein the device is an ultrasound scanner.

5. The system according to claim 1, wherein the calculating device is remote from a device that includes the elastography device.

6. The system according to claim 5, wherein the calculating device is adapted to communicate with the elastography device via Ethernet or Wi-Fi link to receive said values of said physical parameters.

7. The system according to claim 5, wherein the display is part of a computer that is remote from both the calculating device and the elastography device.

8. A method for calculating a score in a patient, said score being a quantitative or semi-quantitative evaluation of liver damage of alcoholic or non-alcoholic steatohepatitis type, the method comprising:
   a) carrying out measurements of physical parameters of the patient with an elastography device, the elastography device configured to generate a shear wave, the elastography device including
      an ultrasonic transducer configured to emit ultrasound shots and to receive corresponding echo signals to track how biological tissues of the patient are moved by the shear wave, the physical parameters including at least liver stiffness and liver ultrasound attenuation associated with the biological tissues,
   b) calculating, with a calculating device in communication with the elastography device, a score parameter representative of liver damage in said patient, the score parameter being based on values of the physical parameters and one or more biological parameters, the calculating device configured to receive the values of said physical parameters from the elastography device and a value of the one or more biological parameters, the one or more biological parameters including at least one transaminase (ASAT or ALAT), said calculating device including one or more processors configured to execute a sequence of instructions for determining the score parameter, and
   c) displaying, with a display in communication with said calculating device, the score parameter, the score parameter being displayed in the form of a numerical value, a binary indicator, a probability or a risk, said score parameter providing an estimate of NASH.

9. The method according to claim 8, wherein the sequence of instruction determine the score parameter according to a logistic regression, a decision tree, a Bayes classifier, or a random forest regression.

10. The method according to claim 8, wherein the calculating device is integrated in a device that includes the elastography device and the display.

11. The method according to claim 8, wherein the device is an ultrasound scanner.

12. A system for calculating a score in a patient, said score being a quantitative or semi-quantitative evaluation of liver damage of alcoholic or non-alcoholic steatohepatitis type, said system comprising:
   a) an elastography device configured to carry out measurements of physical parameters of the patient, the elastography device configured to generate a shear wave, the elastography device including
      an ultrasonic transducer configured to emit ultrasound shots and to receive corresponding echo signals to track how biological tissues of the patient are moved by the shear wave, the physical parameters including at least liver stiffness and liver ultrasound attenuation associated with the biological tissues,
   b) a calculating device configured to receive values of said physical parameters calculated by the elastography device and a value of one or more biological parameters, the one or more biological parameters including at least one transaminase (ASAT or ALAT), said calculating device including one or more microprocessors configured to execute a sequence of instructions for determining a score parameter, based on the values of the physical parameters and the one or more biological parameters, representative of liver damage in said patient, and
   c) a display device including a screen, the display device in communication with said calculating device, said display device configured to display the score parameter on the screen, the score parameter being displayed in the form of a numerical value, a binary indicator, a probability or a risk, said score parameter providing an estimate of NASH.

13. The system according to claim 12, wherein the sequence of instructions determine the score parameter according to a logistic regression, a decision tree, a Bayes classifier, or a random forest regression.

14. The system according to claim 12, wherein the calculating device is adapted to communicate with the elastography device via Ethernet or Wi-Fi link to receive said values of said physical parameters.

15. A method for calculating a score in a patient, said score being a quantitative or semi-quantitative evaluation of liver damage of alcoholic or non-alcoholic steatohepatitis type, the method comprising:
   a) carrying out measurements of physical parameters of the patient with an elastography device, the elastography device configured to generate a shear wave, the elastography device including
      an ultrasonic transducer configured to emit ultrasound shots and to receive corresponding echo signals to track how biological tissues of the patient are moved by the shear wave, the physical parameters including at least liver stiffness and liver ultrasound attenuation associated with the biological tissues,
   b) calculating, with a calculating device, a score parameter representative of liver damage in said patient, the score parameter being based on values of the physical parameters and one or more biological parameters, the calculating device configured to receive the values of said physical parameters calculated by the elastography device and a value of the one or more biological parameters, the one or more biological parameters including at least one transaminase (ASAT or ALAT), said calculating device including one or more microprocessors configured to execute a sequence of instructions for determining the score parameter, and
   c) displaying, with a display device in communication with said calculating device, the score parameter, the score parameter being displayed on a screen of the display device in the form of a numerical value, a binary indicator, a probability or a risk, said score parameter providing an estimate of NASH.

16. The method according to claim 15, wherein the sequence of instructions determine the score parameter according to a logistic regression, a decision tree, a Bayes classifier, or a random forest regression.

17. The method according to claim 15, wherein the calculating device is adapted to communicate with the elastography device via Ethernet or Wi-Fi link to receive said values of said physical parameters.

* * * * *